US009096680B2

(12) United States Patent
Reed et al.

(10) Patent No.: US 9,096,680 B2
(45) Date of Patent: Aug. 4, 2015

(54) MTOR LIGANDS AND POLYNUCLEOTIDES ENCODING MTOR LIGANDS

(71) Applicant: Intrexon Corporation, Blacksburg, VA (US)

(72) Inventors: Thomas David Reed, Arlington, VA (US); Amy H. Atzel, Minneapolis, MN (US)

(73) Assignee: Intrexon Corporation, Blacksburg, VA (US)

(*) Notice: Subject to any disclaimer, the term of this patent is extended or adjusted under 35 U.S.C. 154(b) by 0 days.

(21) Appl. No.: 14/187,930

(22) Filed: Feb. 24, 2014

(65) Prior Publication Data

US 2014/0178931 A1   Jun. 26, 2014

Related U.S. Application Data

(60) Continuation of application No. 13/491,315, filed on Jun. 7, 2012, now Pat. No. 8,679,784, which is a continuation of application No. 12/707,600, filed on Feb. 17, 2010, now Pat. No. 8,211,669, which is a division of application No. 11/947,880, filed on Nov. 30, 2007, now Pat. No. 7,705,122.

(60) Provisional application No. 60/868,539, filed on Dec. 4, 2006.

(51) Int. Cl.
| C12P 21/06 | (2006.01) |
| C07H 21/02 | (2006.01) |
| C07K 14/47 | (2006.01) |

(52) U.S. Cl.
CPC ............. *C07K 14/47* (2013.01); *C07K 14/4702* (2013.01); *C07K 14/4703* (2013.01); *C07K 2319/02* (2013.01); *C07K 2319/41* (2013.01)

(58) Field of Classification Search
CPC .................... C07K 14/4702; C07K 14/4703
USPC ............. 536/23.1; 435/69.1, 320.1, 252.3, 15
See application file for complete search history.

(56) References Cited

U.S. PATENT DOCUMENTS

| 7,071,295 | B2 | 7/2006 | Reed |
| 7,705,122 | B2 | 4/2010 | Reed et al. |
| 7,745,391 | B2* | 6/2010 | Mintz et al. .................. 514/19.3 |
| 7,943,732 | B2 | 5/2011 | Reed |
| 8,153,598 | B2 | 4/2012 | Reed et al. |
| 8,211,669 | B2 | 7/2012 | Reed et al. |
| 8,283,445 | B2 | 10/2012 | Reed et al. |
| 8,575,304 | B2 | 11/2013 | Reed et al. |
| 8,679,784 | B2 | 3/2014 | Reed et al. |
| 2004/0185556 | A1 | 9/2004 | Reed |
| 2008/0032947 | A1 | 2/2008 | Reed |
| 2008/0050808 | A1 | 2/2008 | Reed et al. |
| 2008/0051360 | A1 | 2/2008 | Reed et al. |
| 2008/0213834 | A1 | 9/2008 | Reed et al. |
| 2009/0186379 | A1 | 7/2009 | Reed |
| 2009/0215173 | A1 | 8/2009 | Reed |
| 2009/0215866 | A1 | 8/2009 | Reed |
| 2010/0279378 | A1 | 11/2010 | Bachinsky et al. |

FOREIGN PATENT DOCUMENTS

| WO | WO 2005/040336 A2 | 5/2005 |
| WO | WO 2005/116231 A1 | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Brunn, G., et al., "The Mammalian Target of Rampamycin Phosphorylates Sites Having a (Ser/Thr)-Pro Motif and Is Activated by Antibodies to a Region near Its COOH Terminus," *J. Biol. Chem.* 272:32547-50, The American Society for Biochemistry and Molecular Biology, Inc., United States (1997).

Burnett, P., et al.,"RAFT1 phosphorylation of the translational regulators $p_{70}$ S6 kinase and $_4$E-BP1," *Proc. Natl. Acad. Sci. USA* 95:1432-37, National Academy of Sciences, United States (1998).

Carlson, C., et al., "Mammalian target of rapamycin regulates IRS-1 serine 307 phosphorylation," *Biochem. Biophys. Res. Commun.* 316:533-9, Academic Press, United States (2004).

Carraway, H. and Hidalgo, M., et al., "New targets for therapy in breast cancer Mammalian target of rapamycin (mTOR) antagonists," *Breast Cancer Res.* 6:219-224, BioMed Central, Ltd., United Kingdom (2004).

Gringas, A., et al., "Regulation of 4E-BP1 phosphylation: a novel two-step mechanism," *Genes Dev.* 13:1422-37, Cold Spring Harbor Laboratory Press, United States (1999).

Isotani, S., et al., "Immunopurified Mammalian Target of Rapamycin Phosphorylates and Activates p70 S6 Kinase α in Vitro," *J. Biol. Chem.* 274:34493-8, The American Society for Biochemistry and Molecular Biology, Inc., United States (1999).

Ji, Y., et al., "Targeted Inhibition of $Ca^{2+}$Calmodulin-dependant Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc., United States (2003).

Minami, T., et al., "Distinct regulatory mechanism for p70 S6 kinase β from that for p70 S6 kinase α," *Genes Cells* 6:1003-15, Blackwell Publishing Ltd., United Kingdom (2001).

Mothe-Satney, I., et al., "Mammalian Target of Rapamycin-depedent Phoshorylation of PHAS-I in Four (S/T)P Sites Detected by Phospho-specific Antibodies," *J. Biol. Chem.* 275:33836-43, The American Society for Biochemistry and Molecular Biology, Inc., United States (2000).

(Continued)

*Primary Examiner* — Maryam Monshipouri
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate mTOR activity. The ligands and polyligands are utilized as research tools or as therapeutics. The invention includes linkage of the ligands and polyligands to a cellular localization signal, epitope tag and/or a reporter. The invention also includes polynucleotides encoding the ligands and polyligands.

20 Claims, 12 Drawing Sheets

(56) References Cited

OTHER PUBLICATIONS

Peterson, R., et al., "FKBP12-Rapamycin-associated Protein (FRAP) Autophosphorylates at Serine 2481 under Translationally Repressive Conditions," *J. Biol. Chem.* 275:7416-23, The American Society for Biochemistry and Molecular Biology, Inc., United States (2000).

Yokogami, K., et al., "Serine phosphorylation and maximal activation of STAT3 during CNTF signaling is mediated by the rapamycin target mTOR," *Curr. Biol.* 10:47-50, Elsevier Science Ltd., United Kingdom (2000).

\* cited by examiner

| LIGAND X | LIGAND X |
|---|---|

FIGURE 1A

| LIGAND X | LIGAND X | LIGAND X |
|---|---|---|

FIGURE 1B

| LIGAND X | LIGAND X | LIGAND X | LIGAND X | LIGAND X |
|---|---|---|---|---|

FIGURE 1C

| LIGAND X | SPACER | LIGAND X |
|---|---|---|

FIGURE 2A

| LIGAND X | SPACER | LIGAND X | SPACER | LIGAND X |
|---|---|---|---|---|

FIGURE 2B

| LIGAND X | LIGAND X | SPACER | LIGAND X | SPACER | LIGAND X |
|---|---|---|---|---|---|

FIGURE 2C

| LIGAND X | LIGAND Y |
|---|---|

FIGURE 3A

| LIGAND X | LIGAND Y | LIGAND Z |
|---|---|---|

FIGURE 3B

| LIGAND X | LIGAND Y | LIGAND X | LIGAND Z | LIGAND A |
|---|---|---|---|---|

FIGURE 3C

| LIGAND A | LIGAND B | LIGAND C | LIGAND D |
|---|---|---|---|

FIGURE 3D

| LIGAND A | LIGAND A | LIGAND B | LIGAND C |
|---|---|---|---|

FIGURE 3E

| LIGAND B | SPACER | LIGAND A |

FIGURE 4A

| LIGAND Z | SPACER | LIGAND Y | SPACER | LIGAND X |

FIGURE 4B

| LIGAND X | SPACER | LIGAND Y | SPACER | LIGAND X |

FIGURE 4C

| LIGAND A | SPACER | LIGAND B | SPACER | LIGAND C | SPACER | LIGAND D |

FIGURE 4D

| LIGAND X | SPACER | LIGAND Y | SPACER | LIGAND Z | SPACER | LIGAND E |

FIGURE 4E

| LIGAND C | SPACER | LIGAND Y | SPACER | LIGAND Z | SPACER | LIGAND Y |

FIGURE 4F

| LIGAND X | LIGAND X | EPITOPE |

FIGURE 5A

| EPITOPE | LIGAND X | LIGAND Y |

FIGURE 5B

| LIGAND X | SPACER | LIGAND X | EPITOPE |

FIGURE 5C

| EPITOPE | LIGAND X | SPACER | LIGAND Y |

FIGURE 5D

| LIGAND X | SPACER | LIGAND Y | SPACER | LIGAND A | LIGAND B | EPITOPE |

FIGURE 5E

| EPITOPE | LIGAND X | SPACER | LIGAND Y | LIGAND A | LIGAND B |

FIGURE 5F

| LIGAND X | EPITOPE |

FIGURE 5G

| LIGAND X | LIGAND X | REPORTER |

FIGURE 6A

| REPORTER | LIGAND X | LIGAND Y |

FIGURE 6B

| LIGAND X | SPACER | LIGAND X | REPORTER |

FIGURE 6C

| REPORTER | LIGAND X | SPACER | LIGAND Y |

FIGURE 6D

| LIGAND X | SPACER | LIGAND Y | SPACER | LIGAND A | LIGAND B | REPORTER |

FIGURE 6E

| REPORTER | LIGAND X | SPACER | LIGAND Y | LIGAND A | LIGAND B |

FIGURE 6F

| LIGAND X | REPORTER |

FIGURE 6G

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Y |

FIGURE 7G

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

SEQUENCE LISTING

<160> NUMBER OF SEQ ID NOS: 55

<210> SEQ ID NO 1
<211> LENGTH: 175
<212> TYPE: PRT
<213> ORGANISM: artificial sequence
<220> FEATURE:
<223> OTHER INFORMATION: synthetic

<400> SEQUENCE: 1

Gln Thr Pro Ser Arg Ala Ile Pro Ala Thr Arg Arg Val Val Leu Gly
1               5                   10                  15

Asp Gly Val Gln Leu Pro Pro Gly Asp Tyr Ser Thr Ala Pro Gly Gly
            20                  25                  30

Thr Leu Phe Ser Thr Ala Pro Gly Gly Thr Arg Pro Ala Ala Ala Asp
        35                  40                  45

Pro Leu Leu Asn Trp Arg Leu Met Asp Thr Asn Thr Lys Gly Asn Lys
    50                  55                  60

Arg Ser Arg Thr Arg Ala Asp Ala Tyr Ser Ala Gly Gln Ser Val Glu
65                  70                  75                  80

```
Ile Glu Phe Pro Gly Gly Val Gly Leu Thr Arg Arg Ser Arg Thr
            85                  90                  95

Glu Ala Ile Thr Ala Thr Ser Pro Ala Ser Met Val Pro Ala Gly Ala
            100                 105                 110

Lys Pro Leu Leu Gln Ser Glu Glu Asp Val Ser Gln Phe Asp Ser Lys
            115                 120                 125

Phe Thr Arg Gln Ala Pro Val Asp Ser Pro Asp Asp Ser Thr Leu Ser
            130                 135                 140

Glu Ser Ala Asn Gln Val Phe Leu Gly Phe Ala Tyr Val Ala Pro Ser
145                 150                 155                 160

Val Leu Glu Ser Val Lys Glu Lys Phe Ser Phe Glu Pro Lys Ile
            165                 170                 175

<210> SEQ ID NO 2
<211> LENGTH: 525
<212> TYPE: DNA
<213> ORGANISM: artificial sequence
<220> FEATURE:
<223> OTHER INFORMATION: synthetic

<400> SEQUENCE: 2 cagacccca  gcagggccat  ccccgccacc  aggagggtgg  tgctgggcga  cggcgtgcag    60
ctgccccccg  cgactacag  caccgccccc  ggcggcaccc  tgttcagcac  cgccccggc   120 ggcaccaggc  ccgccgccgc  cgaccccctg  ctgaactgga  ggctgatgga  caccaacacc   180
aagggcaaca  gaggagcag  gaccagggcc  gacgcctaca  gcgccggcca  gagcgtggag   240
atcgaattcc  ccggcggcgg  cgtgggcctg  accaggagga  gcaggaccga  ggccatcacc   300
gccaccagcc  ccgccagcat  ggtgcccgcc  ggcgccaagc  ccctgctgca  gagcgaggag   360
gacgtgagcc  agttcgacag  caagttcacc  aggcaggccc  cgtggacag  ccccgacgac   420 agcaccctga  gcgagagcgc  caaccaggtg  ttcctgggct  cgcctacgt  ggccccagc   480 gtgctggaga  gcgtgaagga  aagttcagc  ttcgagccca  agatc                    525

<210> SEQ ID NO 3
<211> LENGTH: 559
<212> TYPE: DNA
<213> ORGANISM: artificial sequence
<220> FEATURE:
<223> OTHER INFORMATION: synthetic

<400> SEQUENCE: 3
gctagcgccg  ccagacccc  cagcagggcc  atccccgcca  ccaggagggt  ggtgctgggc    60
gacggcgtgc  agctgccccc  cggcgactac  agcaccgccc  ccggcggcac  cctgttcagc   120 accgccccg  cggcaccag  gcccgccgcc  gccgaccccc  tgctgaactg  gaggctgatg   180
gacaccaaca  ccaagggcaa  caagaggagc  aggaccaggg  ccgacgccta  cagcgccggc   240
cagagcgtgg  agatcgaatt  ccccggcggc  ggcgtgggcc  tgaccaggag  gagcaggacc   300
gaggccatca  ccgccaccag  ccccgccagc  atggtgcccg  ccggcgccaa  gcccctgctg   360
cagagcgagg  aggacgtgag  ccagttcgac  agcaagttca  ccaggcaggc  ccccgtggac   420
agccccgacg  acagcaccct  gagcgagagc  gccaaccagg  tgttcctggg  cttcgcctac   480
gtggccccca  gcgtgctgga  gagcgtgaag  gagaagttca  gcttcgagcc  caagatcccc   540
gggggaggcg  gaatcgatt                                                   559

<210> SEQ ID NO 4
```

<211> LENGTH: 173
<212> TYPE: PRT
<213> ORGANISM: artificial sequence
<220> FEATURE:
<223> OTHER INFORMATION: synthetic

<400> SEQUENCE: 4

```
Gln Val Gly Leu Thr Arg Arg Ser Arg Thr Glu Ala Ile Thr Ala Thr
1               5                   10                  15
Ser Pro Ala Ser Met Ala Ala Asp Tyr Ser Thr Ala Pro Gly Gly
            20                  25                  30
Thr Leu Phe Ser Thr Ala Pro Gly Gly Thr Arg Ile Ile Tyr Asp Arg
        35                  40                  45
Lys Phe Leu Met Gly Gly Gly Cys Val Thr Pro Thr Cys Ser
    50                  55                  60
Asn Thr Ile Asp Leu Pro Met Ala Pro Arg Thr Leu Asp Ser Leu Met
65                  70                  75                  80
Gln Ala Ala Ala Val Glu Leu Gly Glu Pro Ala His Lys Lys Thr
                85                  90                  95
Gly Thr Thr Val Pro Glu Ser Ile His Ala Phe Ile Gly Asp Gly Leu
            100                 105                 110
Val Lys Pro Glu Ala Leu Asn Lys Lys Ala Ile Gln Ile Ile Asn Arg
        115                 120                 125
Val Arg Asp Lys Leu Thr Gly Arg Asp Phe Ser His Asp Asp Thr Leu
130                 135                 140
Asp Val Pro Thr Gln Val Glu Leu Leu Ile Lys Gln Ala Thr Ser His
145                 150                 155                 160
Glu Asn Leu Cys Gln Cys Tyr Ile Gly Trp Cys Pro Phe
                165                 170
```

<210> SEQ ID NO 5
<211> LENGTH: 519
<212> TYPE: DNA
<213> ORGANISM: artificial sequence
<220> FEATURE:
<223> OTHER INFORMATION: synthetic

<400> SEQUENCE: 5

```
caggtgggcc tgaccaggag gagcaggacc gaggccatca ccgccaccag ccccgccagc    60
atggccgccg ccgactacag caccgccccc ggcggcaccc tgttcagcac cgccccggc   120
ggcaccagga tcatctacga caggaagttc ctgatgggcg gcggcggctg cgtgaccccc   180
accacctgca gcaacaccat cgacctgccc atggccccta gaacactcga cagcctgatg   240
caggccgccg ccgccgtgga gctgggcgag cccgcccaca agaagaccgg caccaccgtg   300
cccgagagca tccacgcctt catcggcgac ggcctggtga agcccgaggc cctgaacaag   360
aaggccatcc agatcatcaa cagggtgagg gacaagctga ccggcaggga cttcagccac   420
gacgacaccc tggacgtgcc tacacaagtc gagctgctga tcaagcaggc caccagccac   480
gagaacctgt gccagtgcta catcggctgg tgccccttc                          519
```

<210> SEQ ID NO 6
<211> LENGTH: 546
<212> TYPE: DNA
<213> ORGANISM: artificial sequence
<220> FEATURE:
<223> OTHER INFORMATION: synthetic

<400> SEQUENCE: 6

```
gccggccagg tgggcctgac caggaggagc aggaccgagg ccatcaccgc caccagcccc    60
gccagcatgg ccgccgccga ctacagcacc gccccggcg gcaccctgtt cagcaccgcc    120
cccggcggca ccaggatcat ctacgacagg aagttcctga tgggcggcgg cggctgcgtg    180 accccccacca cctgcagcaa caccatcgac ctgcccatgg cccctagaac actcgacagc    240
ctgatgcagg ccgccgccgc cgtggagctg ggcgagcccg cccacaagaa gaccggcacc    300
accgtgcccg agagcatcca cgccttcatc ggcgacggcc tggtgaagcc cgaggccctg    360
aacaagaagg ccatccagat catcaacagg gtgagggaca agctgaccgg cagggacttc    420
agccacgacg acaccctgga cgtgcctaca caagtcgagc tgctgatcaa gcaggccacc    480
agccacgaga acctgtgcca gtgctacatc ggctggtgcc ccttccccgg gggcggaggc    540
atcgat                                                                546
```

```
<210> SEQ ID NO 7
<211> LENGTH: 525
<212> TYPE: PRT
<213> ORGANISM: Homo sapiens
<220> FEATURE:
<221> NAME/KEY: misc_feature
<222> LOCATION: (412)..(412)
<223> OTHER INFORMATION: Xaa can be any naturally occurring amino acid

<400> SEQUENCE: 7
```

Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

```
Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
    370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Xaa Tyr Val Ala Pro
                405                 410                 415

Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
    450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
        515                 520                 525

<210> SEQ ID NO 8
<211> LENGTH: 495
<212> TYPE: PRT
<213> ORGANISM: Homo sapiens
<220> FEATURE:
<221> NAME/KEY: misc_feature
<222> LOCATION: (401)..(401)
<223> OTHER INFORMATION: Xaa can be any naturally occurring amino acid

<400> SEQUENCE: 8

Met Ala Arg Gly Arg Arg Ala Arg Gly Ala Gly Ala Ala Met Ala Ala
1               5                   10                  15

Val Phe Asp Leu Asp Leu Glu Thr Glu Glu Gly Ser Glu Gly Glu Gly
            20                  25                  30

Glu Pro Glu Leu Ser Pro Ala Asp Ala Cys Pro Leu Ala Glu Leu Arg
        35                  40                  45

Ala Ala Gly Leu Glu Pro Val Gly His Tyr Glu Glu Val Glu Leu Thr
    50                  55                  60

Glu Thr Ser Val Asn Val Gly Pro Glu Arg Ile Gly Pro His Cys Phe
65                  70                  75                  80
```

```
Glu Leu Leu Arg Val Leu Gly Lys Gly Gly Tyr Gly Lys Val Phe Gln
                 85                  90                  95

Val Arg Lys Val Gln Gly Thr Asn Leu Gly Lys Ile Tyr Ala Met Lys
            100                 105                 110

Val Leu Arg Lys Ala Lys Ile Val Arg Asn Ala Lys Asp Thr Ala His
        115                 120                 125

Thr Arg Ala Glu Arg Asn Ile Leu Glu Ser Val Lys His Pro Phe Ile
    130                 135                 140

Val Glu Leu Ala Tyr Ala Phe Gln Thr Gly Gly Lys Leu Tyr Leu Ile
145                 150                 155                 160

Leu Glu Cys Leu Ser Gly Gly Glu Leu Phe Thr His Leu Glu Arg Glu
                165                 170                 175

Gly Ile Phe Leu Glu Asp Thr Ala Cys Phe Tyr Leu Ala Glu Ile Thr
            180                 185                 190

Leu Ala Leu Gly His Leu His Ser Gln Gly Ile Ile Tyr Arg Asp Leu
        195                 200                 205

Lys Pro Glu Asn Ile Met Leu Ser Ser Gln Gly His Ile Lys Leu Thr
    210                 215                 220

Asp Phe Gly Leu Cys Lys Glu Ser Ile His Glu Gly Ala Val Thr His
225                 230                 235                 240

Thr Phe Cys Gly Thr Ile Glu Tyr Met Ala Pro Glu Ile Leu Val Arg
                245                 250                 255

Ser Gly His Asn Arg Ala Val Asp Trp Trp Ser Leu Gly Ala Leu Met
            260                 265                 270

Tyr Asp Met Leu Thr Gly Ser Pro Pro Phe Thr Ala Glu Asn Arg Lys
        275                 280                 285

Lys Thr Met Asp Lys Ile Ile Arg Gly Lys Leu Ala Leu Pro Pro Tyr
    290                 295                 300

Leu Thr Pro Asp Ala Arg Asp Leu Val Lys Lys Phe Leu Lys Arg Asn
305                 310                 315                 320

Pro Ser Gln Arg Ile Gly Gly Gly Pro Gly Asp Ala Ala Asp Val Gln
                325                 330                 335

Arg His Pro Phe Phe Arg His Met Asn Trp Asp Asp Leu Leu Ala Trp
            340                 345                 350

Arg Val Asp Pro Pro Phe Arg Pro Cys Leu Gln Ser Glu Glu Asp Val
        355                 360                 365

Ser Gln Phe Asp Thr Arg Phe Thr Arg Gln Thr Pro Val Asp Ser Pro
    370                 375                 380

Asp Asp Thr Ala Leu Ser Glu Ser Ala Asn Gln Ala Phe Leu Gly Phe
385                 390                 395                 400

Xaa Tyr Val Ala Pro Ser Val Leu Asp Ser Ile Lys Glu Gly Phe Ser
                405                 410                 415

Phe Gln Pro Lys Leu Arg Ser Pro Arg Arg Leu Asn Ser Ser Pro Arg
            420                 425                 430

Val Pro Val Ser Pro Leu Lys Phe Ser Pro Phe Glu Gly Phe Arg Pro
        435                 440                 445

Ser Pro Ser Leu Pro Glu Pro Thr Glu Leu Pro Leu Pro Pro Leu Leu
    450                 455                 460

Pro Pro Pro Pro Ser Thr Thr Ala Pro Leu Pro Ile Arg Pro Pro
465                 470                 475                 480

Ser Gly Thr Lys Lys Ser Lys Arg Gly Arg Gly Arg Pro Gly Arg
                485                 490                 495
```

-continued

```
<210> SEQ ID NO 9
<211> LENGTH: 117
<212> TYPE: PRT
<213> ORGANISM: Rattus rattus
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

<400> SEQUENCE: 9

Met Ser Ala Gly Ser Ser Cys Ser Gln Thr Pro Ser Arg Ala Ile Pro
1               5                   10                  15

Thr Arg Arg Val Ala Leu Gly Asp Gly Val Gln Leu Pro Pro Gly Asp
            20                  25                  30

Tyr Ser Thr Xaa Pro Gly Gly Thr Leu Phe Ser Thr Xaa Pro Gly Gly
        35                  40                  45

Thr Arg Ile Ile Tyr Asp Arg Lys Phe Leu Met Glu Cys Arg Asn Xaa
    50                  55                  60

Pro Val Ala Lys Xaa Pro Pro Lys Asp Leu Pro Thr Ile Pro Gly Val
65                  70                  75                  80

Thr Xaa Pro Thr Ser Asp Glu Pro Pro Met Gln Ala Ser Gln Ser His
            85                  90                  95

Leu His Ser Ser Pro Glu Asp Lys Arg Ala Gly Gly Glu Glu Ser Gln
            100                 105                 110

Phe Glu Met Asp Ile
        115

<210> SEQ ID NO 10
<211> LENGTH: 118
<212> TYPE: PRT
<213> ORGANISM: Homo sapiens
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 10

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
            20                  25                  30

Asp Tyr Ser Thr Xaa Pro Gly Gly Thr Leu Phe Ser Thr Xaa Pro Gly
        35                  40                  45

Gly Thr Arg Ile Ile Tyr Asp Arg Lys Phe Leu Met Glu Cys Arg Asn
    50                  55                  60
```

```
Ser Pro Val Thr Lys Thr Pro Pro Arg Asp Leu Pro Thr Ile Pro Gly
 65                  70                  75                  80

Val Thr Ser Pro Ser Ser Asp Glu Pro Pro Met Glu Ala Ser Gln Ser
             85                  90                  95

His Leu Arg Asn Ser Pro Glu Asp Lys Arg Ala Gly Gly Glu Glu Ser
            100                 105                 110

Gln Phe Glu Met Asp Ile
        115
```

<210> SEQ ID NO 11
<211> LENGTH: 770
<212> TYPE: PRT
<213> ORGANISM: Homo sapiens
<220> FEATURE:
<221> NAME/KEY: misc_feature
<222> LOCATION: (727)..(727)
<223> OTHER INFORMATION: Xaa can be any naturally occurring amino acid

<400> SEQUENCE: 11

```
Met Ala Gln Trp Asn Gln Leu Gln Gln Leu Asp Thr Arg Tyr Leu Glu
  1               5                  10                  15

Gln Leu His Gln Leu Tyr Ser Asp Ser Phe Pro Met Glu Leu Arg Gln
             20                  25                  30

Phe Leu Ala Pro Trp Ile Glu Ser Gln Asp Trp Ala Tyr Ala Ala Ser
         35                  40                  45

Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
             85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
```

-continued

```
            290                 295                 300
Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
                370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
                435                 440                 445

Gly Leu Lys Ile Asp Leu Glu Thr His Ser Leu Pro Val Val Val Ile
                450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
                675                 680                 685

Pro Glu Ser Gln Glu His Pro Glu Ala Asp Pro Gly Ser Ala Ala Pro
                690                 695                 700

Tyr Leu Lys Thr Lys Phe Ile Cys Val Thr Pro Thr Thr Cys Ser Asn
705                 710                 715                 720
```

```
Thr Ile Asp Leu Pro Met Xaa Pro Arg Thr Leu Asp Ser Leu Met Gln
                    725                 730                 735

Phe Gly Asn Asn Gly Glu Gly Ala Glu Pro Ser Ala Gly Gly Gln Phe
                740                 745                 750

Glu Ser Leu Thr Phe Asp Met Glu Leu Thr Ser Glu Cys Ala Thr Ser
            755                 760                 765

Pro Met
    770

<210> SEQ ID NO 12
<211> LENGTH: 1242
<212> TYPE: PRT
<213> ORGANISM: Homo sapiens
<220> FEATURE:
<221> NAME/KEY: misc_feature
<222> LOCATION: (307)..(307)
<223> OTHER INFORMATION: Xaa can be any naturally occurring amino acid

<400> SEQUENCE: 12

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285
```

-continued

```
Leu Asn Asn Pro Pro Ser Gln Val Gly Leu Thr Arg Arg Ser Arg
290                 295                 300

Thr Glu Xaa Ile Thr Ala Thr Ser Pro Ala Ser Met Val Gly Lys
305             310                 315                 320

Pro Gly Ser Phe Arg Val Arg Ala Ser Ser Asp Gly Glu Gly Thr Met
            325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
            355                 360                 365

Leu Asn His Ser Arg Ser Ile Pro Met Pro Ala Ser Arg Cys Ser Pro
370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
                405                 410                 415

Ser Gly Ser Pro Ser Asp Gly Gly Phe Ile Ser Ser Asp Glu Tyr Gly
            420                 425                 430

Ser Ser Pro Cys Asp Phe Arg Ser Ser Phe Arg Ser Val Thr Pro Asp
            435                 440                 445

Ser Leu Gly His Thr Pro Pro Ala Arg Gly Glu Glu Glu Leu Ser Asn
450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
            500                 505                 510

Ser Ala Ala Asp Leu Asp Asn Arg Phe Arg Lys Arg Thr His Ser Ala
            515                 520                 525

Gly Thr Ser Pro Thr Ile Thr His Gln Lys Thr Pro Ser Gln Ser Ser
530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
            580                 585                 590

Glu Arg Arg Gly Gly His His Arg Pro Asp Ser Ser Thr Leu His Thr
            595                 600                 605

Asp Asp Gly Tyr Met Pro Met Ser Pro Gly Val Ala Pro Val Pro Ser
610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
            660                 665                 670

Pro Asp Ile Gly Gly Gly Pro Ser Ser Ser Ser Ser Ser Asn Ala
            675                 680                 685

Val Pro Ser Gly Thr Ser Tyr Gly Lys Leu Trp Thr Asn Gly Val Gly
690                 695                 700

Gly His His Ser His Val Leu Pro His Pro Lys Pro Pro Val Glu Ser
```

-continued

```
            705                 710                 715                 720
        Ser Gly Gly Lys Leu Leu Pro Cys Thr Gly Asp Tyr Met Asn Met Ser
                        725                 730                 735
        Pro Val Gly Asp Ser Asn Thr Ser Ser Pro Ser Asp Cys Tyr Tyr Gly
                        740                 745                 750
        Pro Glu Asp Pro Gln His Lys Pro Val Leu Ser Tyr Tyr Ser Leu Pro
                        755                 760                 765
        Arg Ser Phe Lys His Thr Gln Arg Pro Gly Pro Glu Glu Gly Ala
        770                 775                 780
        Arg His Gln His Leu Arg Leu Ser Thr Ser Ser Gly Arg Leu Leu Tyr
        785                 790                 795                 800
        Ala Ala Thr Ala Asp Asp Ser Ser Ser Thr Ser Ser Asp Ser Leu
                        805                 810                 815
        Gly Gly Gly Tyr Cys Gly Ala Arg Leu Glu Pro Ser Leu Pro His Pro
                        820                 825                 830
        His His Gln Val Leu Gln Pro His Leu Pro Arg Lys Val Asp Thr Ala
                        835                 840                 845
        Ala Gln Thr Asn Ser Arg Leu Ala Arg Pro Thr Arg Leu Ser Leu Gly
        850                 855                 860
        Asp Pro Lys Ala Ser Thr Leu Pro Arg Ala Arg Glu Gln Gln Gln Gln
        865                 870                 875                 880
        Gln Gln Pro Leu Leu His Pro Pro Glu Pro Lys Ser Pro Gly Glu Tyr
                        885                 890                 895
        Val Asn Ile Glu Phe Gly Ser Asp Gln Ser Gly Tyr Leu Ser Gly Pro
                        900                 905                 910
        Val Ala Phe His Ser Ser Pro Ser Val Arg Cys Pro Ser Gln Leu Gln
                        915                 920                 925
        Pro Ala Pro Arg Glu Glu Glu Thr Gly Thr Glu Glu Tyr Met Lys Met
                        930                 935                 940
        Asp Leu Gly Pro Gly Arg Arg Ala Ala Trp Gln Glu Ser Thr Gly Val
        945                 950                 955                 960
        Glu Met Gly Arg Leu Gly Pro Ala Pro Pro Gly Ala Ala Ser Ile Cys
                        965                 970                 975
        Arg Pro Thr Arg Ala Val Pro Ser Ser Arg Gly Asp Tyr Met Thr Met
                        980                 985                 990
        Gln Met Ser Cys Pro Arg Gln Ser  Tyr Val Asp Thr Ser  Pro Ala Ala
                        995                 1000                1005
        Pro Val  Ser Tyr Ala Asp Met  Arg Thr Gly Ile Ala  Ala Glu Glu
            1010                1015                1020
        Val Ser  Leu Pro Arg Ala Thr  Met Ala Ala Ala Ser  Ser Ser Ser
            1025                1030                1035
        Ala Ala  Ser Ala Ser Pro Thr  Gly Pro Gln Gly Ala  Ala Glu Leu
            1040                1045                1050
        Ala Ala  His Ser Ser Leu Leu  Gly Gly Pro Gln Gly  Pro Gly Gly
            1055                1060                1065
        Met Ser  Ala Phe Thr Arg Val  Asn Leu Ser Pro Asn  Arg Asn Gln
            1070                1075                1080
        Ser Ala  Lys Val Ile Arg Ala  Asp Pro Gln Gly Cys  Arg Arg Arg
            1085                1090                1095
        His Ser  Ser Glu Thr Phe Ser  Ser Thr Pro Ser Ala  Thr Arg Val
            1100                1105                1110
        Gly Asn  Thr Val Pro Phe Gly  Ala Gly Ala Ala Val  Gly Gly Gly
            1115                1120                1125
```

```
Gly Gly Ser Ser Ser Ser Glu Asp Val Lys Arg His Ser Ser
        1130            1135                1140

Ala Ser Phe Glu Asn Val Trp Leu Arg Pro Gly Glu Leu Gly Gly
    1145                1150                1155

Ala Pro Lys Glu Pro Ala Lys Leu Cys Gly Ala Ala Gly Gly Leu
    1160                1165                1170

Glu Asn Gly Leu Asn Tyr Ile Asp Leu Asp Leu Val Lys Asp Phe
    1175                1180                1185

Lys Gln Cys Pro Gln Glu Cys Thr Pro Glu Pro Gln Pro Pro Pro
    1190                1195                1200

Pro Pro Pro Pro His Gln Pro Leu Gly Ser Gly Glu Ser Ser Ser
    1205                1210                1215

Thr Arg Arg Ser Ser Glu Asp Leu Ser Ala Tyr Ala Ser Ile Ser
    1220                1225                1230

Phe Gln Lys Gln Pro Glu Asp Arg Gln
    1235                1240

<210> SEQ ID NO 13
<211> LENGTH: 2549
<212> TYPE: PRT
<213> ORGANISM: Homo sapiens
<220> FEATURE:
<221> NAME/KEY: misc_feature
<222> LOCATION: (2481)..(2481)
<223> OTHER INFORMATION: Xaa can be any naturally occurring amino acid

<400> SEQUENCE: 13

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
                20                  25                  30

Asn Glu Glu Thr Arg Ala Lys Ala Ala Lys Glu Leu Gln His Tyr Val
            35                  40                  45

Thr Met Glu Leu Arg Glu Met Ser Gln Glu Glu Ser Thr Arg Phe Tyr
        50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220
```

```
Pro Lys Glu Met Gln Lys Pro Gln Trp Tyr Arg His Thr Phe Glu
225                 230                 235                 240

Ala Glu Lys Gly Phe Asp Glu Thr Leu Ala Lys Glu Lys Gly Met Asn
            245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
        290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
```

-continued

```
            645                 650                 655
Ser Lys Leu Leu Val Gly Ile Thr Asp Pro Asp Pro Asp Ile Arg
            660                 665                 670
Tyr Cys Val Leu Ala Ser Leu Asp Glu Arg Phe Asp Ala His Leu Ala
            675                 680                 685
Gln Ala Glu Asn Leu Gln Ala Leu Phe Val Ala Leu Asn Asp Gln Val
            690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
                    725                 730                 735
Ile Leu Thr Glu Leu Glu His Ser Gly Ile Gly Arg Ile Lys Glu Gln
            740                 745                 750
Ser Ala Arg Met Leu Gly His Leu Val Ser Asn Ala Pro Arg Leu Ile
            755                 760                 765
Arg Pro Tyr Met Glu Pro Ile Leu Lys Ala Leu Ile Leu Lys Leu Lys
            770                 775                 780
Asp Pro Asp Pro Asp Pro Asn Pro Gly Val Ile Asn Asn Val Leu Ala
785                 790                 795                 800
Thr Ile Gly Glu Leu Ala Gln Val Ser Gly Leu Glu Met Arg Lys Trp
                    805                 810                 815
Val Asp Glu Leu Phe Ile Ile Met Asp Met Leu Gln Asp Ser Ser
            820                 825                 830
Leu Leu Ala Lys Arg Gln Val Ala Leu Trp Thr Leu Gly Gln Leu Val
            835                 840                 845
Ala Ser Thr Gly Tyr Val Val Glu Pro Tyr Arg Lys Tyr Pro Thr Leu
850                 855                 860
Leu Glu Val Leu Leu Asn Phe Leu Lys Thr Gln Asn Gln Gly Thr
865                 870                 875                 880
Arg Arg Glu Ala Ile Arg Val Leu Gly Leu Leu Gly Ala Leu Asp Pro
                    885                 890                 895
Tyr Lys His Lys Val Asn Ile Gly Met Ile Asp Gln Ser Arg Asp Ala
            900                 905                 910
Ser Ala Val Ser Leu Ser Glu Ser Lys Ser Ser Gln Asp Ser Ser Asp
            915                 920                 925
Tyr Ser Thr Ser Glu Met Leu Val Asn Met Gly Asn Leu Pro Leu Asp
            930                 935                 940
Glu Phe Tyr Pro Ala Val Ser Met Val Ala Leu Met Arg Ile Phe Arg
945                 950                 955                 960
Asp Gln Ser Leu Ser His His His Thr Met Val Val Gln Ala Ile Thr
                    965                 970                 975
Phe Ile Phe Lys Ser Leu Gly Leu Lys Cys Val Gln Phe Leu Pro Gln
            980                 985                 990
Val Met Pro Thr Phe Leu Asn Val Ile Arg Val Cys Asp Gly Ala Ile
            995                 1000                1005
Arg Glu Phe Leu Phe Gln Gln Leu Gly Met Leu Val Ser Phe Val
            1010                1015                1020
Lys Ser His Ile Arg Pro Tyr Met Asp Glu Ile Val Thr Leu Met
            1025                1030                1035
Arg Glu Phe Trp Val Met Asn Thr Ser Ile Gln Ser Thr Ile Ile
            1040                1045                1050
Leu Leu Ile Glu Gln Ile Val Val Ala Leu Gly Gly Glu Phe Lys
            1055                1060                1065
```

-continued

```
Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
    1265                1270                1275

Asp Trp Leu Glu Trp Leu Arg Arg Leu Ser Leu Glu Leu Leu Lys
    1280                1285                1290

Asp Ser Ser Ser Pro Ser Leu Arg Ser Cys Trp Ala Leu Ala Gln
    1295                1300                1305

Ala Tyr Asn Pro Met Ala Arg Asp Leu Phe Asn Ala Ala Phe Val
    1310                1315                1320

Ser Cys Trp Ser Glu Leu Asn Glu Asp Gln Gln Asp Glu Leu Ile
    1325                1330                1335

Arg Ser Ile Glu Leu Ala Leu Thr Ser Gln Asp Ile Ala Glu Val
    1340                1345                1350

Thr Gln Thr Leu Leu Asn Leu Ala Glu Phe Met Glu His Ser Asp
    1355                1360                1365

Lys Gly Pro Leu Pro Leu Arg Asp Asp Asn Gly Ile Val Leu Leu
    1370                1375                1380

Gly Glu Arg Ala Ala Lys Cys Arg Ala Tyr Ala Lys Ala Leu His
    1385                1390                1395

Tyr Lys Glu Leu Glu Phe Gln Lys Gly Pro Thr Pro Ala Ile Leu
    1400                1405                1410

Glu Ser Leu Ile Ser Ile Asn Asn Lys Leu Gln Gln Pro Glu Ala
    1415                1420                1425

Ala Ala Gly Val Leu Glu Tyr Ala Met Lys His Phe Gly Glu Leu
    1430                1435                1440

Glu Ile Gln Ala Thr Trp Tyr Glu Lys Leu His Glu Trp Glu Asp
    1445                1450                1455
```

```
Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Thr Ala Ser Thr Glu Gly Ser Asn
1835                1840                1845

Ser Glu Ser Glu Ala Glu Ser Thr Glu Asn Ser Pro Thr Pro Ser
```

-continued

```
            1850                1855                1860
Pro Leu Gln Lys Lys Val Thr Glu Asp Leu Ser Lys Thr Leu Leu
    1865                1870                1875
Met Tyr Thr Val Pro Ala Val Gln Gly Phe Phe Arg Ser Ile Ser
    1880                1885                1890
Leu Ser Arg Gly Asn Asn Leu Gln Asp Thr Leu Arg Val Leu Thr
    1895                1900                1905
Leu Trp Phe Asp Tyr Gly His Trp Pro Asp Val Asn Glu Ala Leu
    1910                1915                1920
Val Glu Gly Val Lys Ala Ile Gln Ile Asp Thr Trp Leu Gln Val
    1925                1930                1935
Ile Pro Gln Leu Ile Ala Arg Ile Asp Thr Pro Arg Pro Leu Val
    1940                1945                1950
Gly Arg Leu Ile His Gln Leu Leu Thr Asp Ile Gly Arg Tyr His
    1955                1960                1965
Pro Gln Ala Leu Ile Tyr Pro Leu Thr Val Ala Ser Lys Ser Thr
    1970                1975                1980
Thr Thr Ala Arg His Asn Ala Ala Asn Lys Ile Leu Lys Asn Met
    1985                1990                1995
Cys Glu His Ser Asn Thr Leu Val Gln Gln Ala Met Met Val Ser
    2000                2005                2010
Glu Glu Leu Ile Arg Val Ala Ile Leu Trp His Glu Met Trp His
    2015                2020                2025
Glu Gly Leu Glu Glu Ala Ser Arg Leu Tyr Phe Gly Glu Arg Asn
    2030                2035                2040
Val Lys Gly Met Phe Glu Val Leu Glu Pro Leu His Ala Met Met
    2045                2050                2055
Glu Arg Gly Pro Gln Thr Leu Lys Glu Thr Ser Phe Asn Gln Ala
    2060                2065                2070
Tyr Gly Arg Asp Leu Met Glu Ala Gln Glu Trp Cys Arg Lys Tyr
    2075                2080                2085
Met Lys Ser Gly Asn Val Lys Asp Leu Thr Gln Ala Trp Asp Leu
    2090                2095                2100
Tyr Tyr His Val Phe Arg Arg Ile Ser Lys Gln Leu Pro Gln Leu
    2105                2110                2115
Thr Ser Leu Glu Leu Gln Tyr Val Ser Pro Lys Leu Leu Met Cys
    2120                2125                2130
Arg Asp Leu Glu Leu Ala Val Pro Gly Thr Tyr Asp Pro Asn Gln
    2135                2140                2145
Pro Ile Ile Arg Ile Gln Ser Ile Ala Pro Ser Leu Gln Val Ile
    2150                2155                2160
Thr Ser Lys Gln Arg Pro Arg Lys Leu Thr Leu Met Gly Ser Asn
    2165                2170                2175
Gly His Glu Phe Val Phe Leu Leu Lys Gly His Glu Asp Leu Arg
    2180                2185                2190
Gln Asp Glu Arg Val Met Gln Leu Phe Gly Leu Val Asn Thr Leu
    2195                2200                2205
Leu Ala Asn Asp Pro Thr Ser Leu Arg Lys Asn Leu Ser Ile Gln
    2210                2215                2220
Arg Tyr Ala Val Ile Pro Leu Ser Thr Asn Ser Gly Leu Ile Gly
    2225                2230                2235
Trp Val Pro His Cys Asp Thr Leu His Ala Leu Ile Arg Asp Tyr
    2240                2245                2250
```

```
Arg Glu Lys Lys Lys Ile Leu Leu Asn Ile Glu His Arg Ile Met
    2255                2260                2265

Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Xaa Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 14
<211> LENGTH: 88
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 14

Val Glu Leu Gly Glu Pro Ala His Lys Lys Thr Gly Thr Thr Val Pro
1               5                   10                  15

Glu Ser Ile His Xaa Phe Ile Gly Asp Gly Leu Val Lys Pro Glu Ala
```

```
                    20                  25                  30
Leu Asn Lys Lys Ala Ile Gln Ile Ile Asn Arg Val Arg Asp Lys Leu
            35                  40                  45

Thr Gly Arg Asp Phe Ser His Asp Asp Thr Leu Asp Val Pro Thr Gln
        50                  55                  60

Val Glu Leu Leu Ile Lys Gln Ala Thr Ser His Glu Asn Leu Cys Gln
65                  70                  75                  80

Cys Tyr Ile Gly Trp Cys Pro Phe
                85

<210> SEQ ID NO 15
<211> LENGTH: 25
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 15

Cys Val Thr Pro Thr Thr Cys Ser Asn Thr Ile Asp Leu Pro Met Xaa
1               5                   10                  15

Pro Arg Thr Leu Asp Ser Leu Met Gln
            20                  25

<210> SEQ ID NO 16
<211> LENGTH: 28
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 16

Asp Tyr Ser Thr Xaa Pro Gly Gly Thr Leu Phe Ser Thr Xaa Pro Gly
1               5                   10                  15

Gly Thr Arg Ile Ile Tyr Asp Arg Lys Phe Leu Met
            20                  25

<210> SEQ ID NO 17
<211> LENGTH: 31
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 17

Val Val Leu Gly Asp Gly Val Gln Leu Pro Pro Gly Asp Tyr Ser Thr
1               5                   10                  15
```

```
Xaa Pro Gly Gly Thr Leu Phe Ser Thr Xaa Pro Gly Gly Thr Arg
         20                  25                  30
```

<210> SEQ ID NO 18
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

```
Ser Thr Xaa Pro Gly Gly Thr Arg
1               5
```

<210> SEQ ID NO 19
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 19

```
Phe Leu Met Glu Cys Arg Asn Xaa Pro Val Ala Lys
1               5                  10
```

<210> SEQ ID NO 20
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

```
Ser Thr Xaa Pro Gly Gly Thr Arg Ile
1               5
```

<210> SEQ ID NO 21
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 21

```
Ser Thr Xaa Pro Gly Gly Thr Leu Phe
1               5
```

<210> SEQ ID NO 22
<211> LENGTH: 43
<212> TYPE: PRT
<213> ORGANISM: artificial sequence
<220> FEATURE:
<223> OTHER INFORMATION: synthetic
<220> FEATURE:

```
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 22

Gln Thr Pro Ser Arg Ala Ile Pro Ala Thr Arg Arg Val Val Leu Gly
1               5                   10                  15

Asp Gly Val Gln Leu Pro Pro Gly Asp Tyr Ser Thr Xaa Pro Gly Gly
            20                  25                  30

Thr Leu Phe Ser Thr Xaa Pro Gly Gly Thr Arg
        35                  40

<210> SEQ ID NO 23
<211> LENGTH: 41
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 23

His His Leu Asn Asn Pro Pro Ser Gln Val Gly Leu Thr Arg Arg
1               5                   10                  15

Ser Arg Thr Glu Xaa Ile Thr Ala Thr Ser Pro Ala Ser Met Val Gly
            20                  25                  30

Gly Lys Pro Gly Ser Phe Arg Tyr Arg
        35                  40

<210> SEQ ID NO 24
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 24

Val Gly Leu Thr Arg Arg Ser Arg Thr Glu Xaa Ile Thr Ala Thr Ser
1               5                   10                  15

Pro Ala Ser Met Val
            20

<210> SEQ ID NO 25
<211> LENGTH: 27
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 25
```

Gly Arg Lys Gly Ser Gly Asp Tyr Met Pro Met Xaa Pro Lys Xaa Val
1               5                   10                  15

Ser Ala Pro Gln Gln Ile Ile Asn Pro Ile Arg
            20                  25

<210> SEQ ID NO 26
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 26

Gln Val Gly Leu Thr Arg Arg Ser Arg Thr Glu Xaa Ile Thr Ala Thr
1               5                   10                  15

Ser Pro Ala Ser Met
            20

<210> SEQ ID NO 27
<211> LENGTH: 41
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 27

Lys Pro Leu Leu Gln Ser Glu Glu Asp Val Ser Gln Phe Asp Ser Lys
1               5                   10                  15

Phe Thr Arg Gln Xaa Pro Val Asp Ser Pro Asp Asp Ser Thr Leu Ser
                20                  25                  30

Glu Ser Ala Asn Gln Val Phe Leu Gly
        35                  40

<210> SEQ ID NO 28
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 28

Ser Gln Phe Asp Ser Lys Phe Thr Arg Gln Xaa Pro Val Asp Ser Pro
1               5                   10                  15

Asp Asp Ser Thr Leu
            20

<210> SEQ ID NO 29
<211> LENGTH: 41
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 29

Val Asp Ser Pro Asp Ser Thr Leu Ser Glu Ser Ala Asn Gln Val
1               5                   10                  15

Phe Leu Gly Phe Xaa Tyr Val Ala Pro Ser Val Leu Glu Ser Val Lys
            20                  25                  30

Glu Lys Phe Ser Phe Glu Pro Lys Ile
        35                  40

<210> SEQ ID NO 30
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 30

Glu Ser Ala Asn Gln Val Phe Leu Gly Phe Xaa Tyr Val Ala Pro Ser
1               5                   10                  15

Val Leu Glu Ser Val
            20

<210> SEQ ID NO 31
<211> LENGTH: 63
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 31

Lys Pro Leu Leu Gln Ser Glu Glu Asp Val Ser Gln Phe Asp Ser Lys
1               5                   10                  15

Phe Thr Arg Gln Xaa Pro Val Asp Ser Pro Asp Asp Ser Thr Leu Ser
            20                  25                  30

Glu Ser Ala Asn Gln Val Phe Leu Gly Phe Xaa Tyr Val Ala Pro Ser
        35                  40                  45

Val Leu Glu Ser Val Lys Glu Lys Phe Ser Phe Glu Pro Lys Ile
    50                  55                  60

<210> SEQ ID NO 32
<211> LENGTH: 43
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 32

Ser Gln Phe Asp Ser Lys Phe Thr Arg Gln Xaa Pro Val Asp Ser Pro
1               5                   10                  15

Asp Asp Ser Thr Leu Ser Glu Ser Ala Asn Gln Val Phe Leu Gly Phe
            20                  25                  30

Xaa Tyr Val Ala Pro Ser Val Leu Glu Ser Val
        35                  40

<210> SEQ ID NO 33
<211> LENGTH: 41
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 33

Lys Thr Lys Phe Ile Cys Val Thr Pro Thr Thr Cys Ser Asn Thr Ile
1               5                   10                  15

Asp Leu Pro Met Xaa Pro Arg Thr Leu Asp Ser Leu Met Gln Phe Gly
            20                  25                  30

Asn Asn Gly Glu Gly Ala Glu Pro Ser
        35                  40

<210> SEQ ID NO 34
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 34

Phe Leu Gly Phe Xaa Tyr Val Ala Pro Ser
1               5                   10

<210> SEQ ID NO 35
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 35

Asn Gln Val Phe Leu Gly Phe Xaa Tyr Val Ala Pro Ser Val Leu Glu
1               5                   10                  15

<210> SEQ ID NO 36
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)

<223> OTHER INFORMATION: Xaa can be any naturally occurring amino acid

<400> SEQUENCE: 36

Ala Asn Gln Ala Phe Leu Gly Phe Xaa Tyr Val Ala Pro Ser Val Leu
1               5                   10                  15

Asp Ser Ile Lys
            20

<210> SEQ ID NO 37
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 37

Gly Asp Tyr Ser Thr Xaa Pro Gly Gly Thr Leu Phe
1               5                   10

<210> SEQ ID NO 38
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 38

Phe Ser Thr Xaa Pro Gly Gly Thr Arg Ile
1               5                   10

<210> SEQ ID NO 39
<211> LENGTH: 35
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 39

Gly Val Gln Leu Pro Pro Gly Asp Tyr Ser Thr Xaa Pro Gly Gly Thr
1               5                   10                  15

Leu Phe Ser Thr Xaa Pro Gly Gly Thr Arg Ile Ile Tyr Asp Arg Lys
            20                  25                  30

Phe Leu Met
        35

<210> SEQ ID NO 40
<211> LENGTH: 32
<212> TYPE: PRT
<213> ORGANISM: artificial sequence
<220> FEATURE:
<223> OTHER INFORMATION: synthetic
<220> FEATURE:

```
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 40

Met Glu Cys Arg Asn Xaa Pro Val Ala Lys Xaa Pro Pro Lys Asp Leu
1               5                   10                  15

Pro Thr Ile Pro Gly Val Thr Xaa Pro Thr Ser Asp Glu Pro Pro Met
            20                  25                  30

<210> SEQ ID NO 41
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 41

Lys Asp Leu Pro Thr Ile Pro Gly Val Thr Xaa Pro Thr Ser Asp Glu
1               5                   10                  15

Pro Pro Met

<210> SEQ ID NO 42
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 42

Pro Val Ala Lys Xaa Pro Pro Lys Asp Leu Pro Thr Ile Pro Gly Val
1               5                   10                  15

<210> SEQ ID NO 43
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 43

Met Glu Cys Arg Asn Xaa Pro Val Ala Lys
1               5                   10

<210> SEQ ID NO 44
<211> LENGTH: 10
<212> TYPE: PRT
<213> ORGANISM: artificial sequence
<220> FEATURE:
```

```
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 44

Asp Leu Pro Met Xaa Pro Arg Thr Leu Asp
1               5                   10

<210> SEQ ID NO 45
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 45

Asn Thr Ile Asp Leu Pro Met Xaa Pro Arg Thr Leu Asp Ser Leu Met
1               5                   10                  15

<210> SEQ ID NO 46
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 46

Arg Arg Ser Arg Thr Glu Xaa Ile Thr Ala
1               5                   10

<210> SEQ ID NO 47
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 47

Gly Leu Thr Arg Arg Ser Arg Thr Glu Xaa Ile Thr Ala Thr Ser Pro
1               5                   10                  15

Ala Ser Met

<210> SEQ ID NO 48
<211> LENGTH: 41
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
```

```
<400> SEQUENCE: 48

Arg Val Val Leu Gly Asp Gly Val Gln Leu Pro Pro Gly Asp Tyr Ser
1               5                   10                  15

Thr Xaa Pro Gly Gly Thr Leu Phe Ser Thr Xaa Pro Gly Gly Thr Arg
            20                  25                  30

Ile Ile Tyr Asp Arg Lys Phe Leu Met
            35                  40

<210> SEQ ID NO 49
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 49

Val Gln Leu Pro Pro Gly Asp Tyr Ser Thr Xaa Pro Gly Gly Thr Leu
1               5                   10                  15

<210> SEQ ID NO 50
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 50

Phe Ser Thr Xaa Pro Gly Gly Thr Arg Ile Ile Tyr Asp Arg Lys
1               5                   10                  15

<210> SEQ ID NO 51
<211> LENGTH: 42
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 51

Val Glu Leu Gly Glu Pro Ala His Lys Lys Thr Gly Thr Thr Val Pro
1               5                   10                  15

Glu Ser Ile His Xaa Phe Ile Gly Asp Gly Leu Val Lys Pro Glu Ala
            20                  25                  30

Leu Asn Lys Lys Ala Ile Gln Ile Ile Asn
            35                  40

<210> SEQ ID NO 52
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (15)..(15)
```

```
<223> OTHER INFORMATION: Xaa can be any naturally occurring amino acid

<400> SEQUENCE: 52

Ala His Lys Lys Thr Gly Thr Thr Val Pro Glu Ser Ile His Xaa Phe
1               5                   10                  15

Ile Gly Asp Gly Leu Val Lys Pro Glu Ala Leu Asn Lys
            20                  25

<210> SEQ ID NO 53
<211> LENGTH: 14
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 53

Val Pro Glu Ser Ile His Xaa Phe Ile Gly Asp Gly Leu Val
1               5                   10

<210> SEQ ID NO 54
<211> LENGTH: 34
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 54

Asp Pro Leu Leu Asn Trp Arg Leu Met Asp Thr Asn Thr Lys Gly Asn
1               5                   10                  15

Lys Arg Ser Arg Thr Arg Xaa Asp Xaa Tyr Ser Ala Gly Gln Ser Val
            20                  25                  30

Glu Ile

<210> SEQ ID NO 55
<211> LENGTH: 62
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 55

His Lys Asp Ser Val Met Ala Val Leu Glu Ala Phe Val Tyr Asp Pro
1               5                   10                  15

Leu Leu Asn Trp Arg Leu Met Asp Thr Asn Thr Lys Gly Asn Lys Arg
            20                  25                  30

Ser Arg Thr Arg Xaa Asp Xaa Tyr Ser Ala Gly Gln Ser Val Glu Ile
        35                  40                  45
```

```
Leu Asp Gly Val Glu Leu Gly Glu Pro Ala His Lys Lys Thr
 50                  55                  60
```

MTOR LIGANDS AND POLYNUCLEOTIDES ENCODING MTOR LIGANDS

This application claims benefit of priority to U.S. provisional application 60/868,539, filed Dec. 4, 2006, the contents of which are incorporated by reference herein.

REFERENCE TO SEQUENCE LISTING SUBMITTED ELECTRONICALLY VIA EFS-WEB

This application includes a "Sequence List.txt," 78,621 bytes, created on Feb. 21, 2014, and submitted electronically via EFS-Web, which is hereby incorporated by reference in its entirety.

FIELD OF INVENTION

The invention relates to mammalian kinase ligands, substrates and modulators. In particular, the invention relates to polypeptides, polypeptide compositions and polynucleotides that encode polypeptides that are ligands, substrates, and/or modulators of mTOR. The invention also relates to polyligands that are homopolyligands or heteropolyligands that modulate mTOR activity. The invention also relates to ligands and polyligands tethered to a subcellular location.

This application has subject matter related to application Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

BACKGROUND OF THE INVENTION

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Rapamycin is a triene macrolide antibiotic, produced by *Streptomyces hygroscopicus*, and which demonstrates anti-fungal, anti-inflammatory, anti-tumor and immunosuppressive properties. Rapamycin also indirectly inhibits the activity of the protein, mTOR, (mammalian target of rapamycin) which, under abnormal conditions, can promote tumor growth. There are two rapamycin analogs, RAD001 and CCI-779, that have shown anticancer activity in clinical trials. It is also desirable to develop direct inhibitors of mTOR as potential therapeutics.

Mammalian target of rapamycin (mTOR), RAFT1, and FRAP are the same enzyme, herein referred to as mTOR. mTOR can phosphorylate serine and threonine residues in protein or peptide substrates. Some cellular substrates of mTOR have been identified and are referenced in Brunn et al. 1997 J Biol Chem 272:32547-50; Burnett et al. 1998 Proc Nati Acad Sci USA 95:1432-7; Carlson et al. 2004 Biochem Biophys Res Commun 316:533-9; Carraway et al. 2004 Breast Cancer Res, 6:219-224; Gringas et al. 1999 Genes & Dev 13:1422-37; Isotani et al. 1999 J Biol Chem 274:34493-8; Minami et al. 2001 Genes to Cells 6:1003-15; Mothe-Satney et al. 2000 J Biol Chem 275:33836-43; Peterson et al. 2000 J Biol Chem 275:7416-23; Yokogami et al. 2000 Current Biology 10:47-50. While individual substrates or ligands have been identified and studied, mixed ligands linked together as polyligands that modulate mTOR activity have not been demonstrated before this invention. An aspect of the invention is to provide novel, modular, inhibitors of mTOR activity by modifying one or more natural substrates by truncation and/or by amino acid substitution. A further aspect of the invention is the subcellular localization of an mTOR inhibitor, ligand, or polyligand by linking to a subcellular localization signal.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

DETAILED DESCRIPTION OF POLYPEPTIDE AND POLYNUCLEOTIDE SEQUENCES

SEQ ID NOS:1-6 are example polyligands and polynucleotides encoding them.

Specifically, the mTOR polyligand of SEQ ID NO:1 is encoded by SEQ ID NO:2 and SEQ ID NO:3, wherein the codons have been optimized for mammalian expression. SEQ ID NO:3 includes flanking restriction sites. SEQ ID NO:1 is an embodiment of a polyligand of the structure A-S1-B-S2-C-S3-D, wherein A is SEQ ID NO:22, B is SEQ ID NO:54, C is SEQ ID NO:24, and D is SEQ ID NO:31, wherein Xaa is alanine, and wherein S1 is a spacer of the amino acid sequence PAAA, and S2 is a spacer of amino acid sequence EFPGGG, and S3 is a spacer of the amino acid sequence PAGA. A polyligand of structure A-S1-B-S2-C-S3-D is also called herein a heteropolyligand, shown generically in FIG. 4D.

SEQ ID NO:4 is an embodiment of a polyligand of the structure X-S4-Y-S5-Z-S6-E, wherein X is SEQ ID NO:23, Y is SEQ ID NO:16, Z is SEQ ID NO:15, and E is SEQ ID NO:14, wherein Xaa is alanine, and wherein S4 is a spacer of amino acid sequence AAA, S5 is a spacer of the amino acid sequence GGGG, and S6 is a spacer of the amino acid sequence AAAA. The mTOR polyligand of SEQ ID NO:4 is encoded by SEQ ID NO:5 and by SEQ ID NO:6, wherein the codons have been optimized for mammalian expression. SEQ ID NO:6 includes flanking restriction sites. A polyligand of structure X-S4-Y-S5-Z-S6-E is also called herein a heteropolyligand, shown generically in FIG. 4E.

SEQ ID NOS:7-13 are full length mTOR protein substrates. These sequences have the following public database accession numbers: NP003152, BAA34402, NP446309, NP644805, AAB27175, NP_004086, and P42345. Each of the sequences represented by these accession numbers is incorporated by reference herein. In SEQ ID NOS:7-13, the positions of the amino acid(s) phosphorylatable by mTOR are represented by Xaa. In wild-type proteins, Xaa is serine or threonine. In the ligands of the invention, Xaa is any amino acid.

SEQ ID NOS:14-55 are peptide subsequences or partial sequences of SEQ ID NOS:7-13, which represent examples of kinase active site blocker peptide ligand sequences where the location of the mTOR phosphorylatable serine or threonine in the natural polypeptide is designated as Xaa.

SEQ ID NOS:14-55 represent examples of monomeric polypeptide ligand sequences.

Amino acid sequences containing Xaa encompass polypeptides where Xaa is any amino acid.

DETAILED DESCRIPTION OF DRAWINGS

FIGS. 1A-4C show examples of homopolymeric ligands without spacers.

FIGS. 2A-2C show examples of homopolymeric ligands with spacers.

FIGS. 3A-3E show examples of heteropolymeric ligands without spacers.

FIGS. 4A-4F show examples of heteropolymeric ligands with spacers.

FIGS. 5A-5G show examples of ligands and polymeric ligands linked to an optional epitope tag.

FIGS. 6A-6G show examples of ligands and polymeric ligands linked to an optional reporter.

FIGS. 7A-7G show examples of ligands and polymeric ligands linked to an optional localization signal.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

BRIEF DESCRIPTION OF THE INVENTION

Figure 10A:
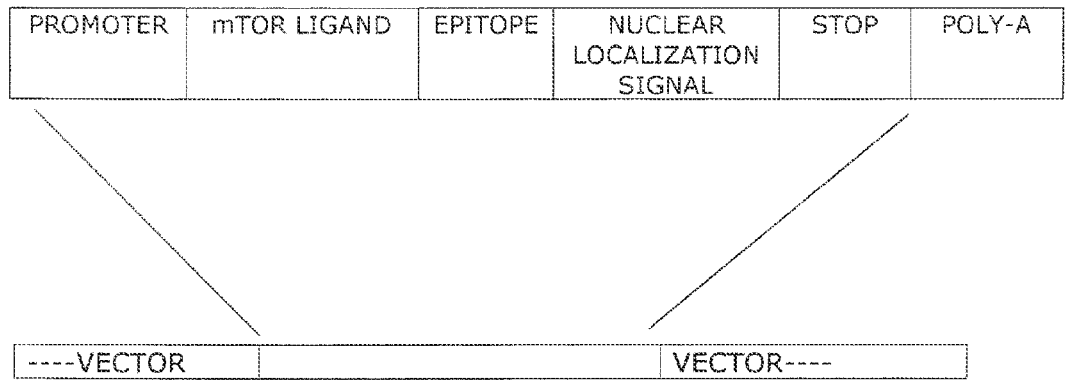
FIGS. 10A-10D show examples of vectors containing ligand gene constructs.

The invention relates to polypeptide ligands and polyligands for mTOR. Various embodiments of the mTOR ligands and polyligands are represented in SEQ ID NOS:1-55. More specifically, the invention relates to ligands, homopolyligands, and heteropolyligands that comprise any one or more of SEQ ID NOS:14-55. Additionally, the invention relates to ligands and polyligands comprising one or more subsequences (partial sequences) of SEQ ID NOS:7-13 or any portion thereof. Furthermore, the invention relates to polyligands with at least about 80%, 85%, 90%, 95%, 96%, 97%, 98% and 99% sequence identity to a polyligand comprising one or more of SEQ ID NOS:14-55 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NOS:7-13.

Polyligands, which can be homopolyligands or heteropolyligands, are chimeric ligands composed of two or more monomeric polypeptide ligands. An example of a monomeric ligand is the polypeptide represented by SEQ ID NO:19, wherein Xaa is any amino acid. SEQ ID NO:19 is a selected subsequence of wild-type full length SEQ ID NO:10, wherein the amino acid corresponding to Xaa in the wild-type sequence is a serine or threonine phosphorylatable by mTOR. An example of a homopolyligand is a polypeptide comprising a dimer or multimer of SEQ ID NO:19, wherein Xaa is any amino acid. An example of a heteropolyligand is a polypeptide comprising SEQ ID NO:14 and one or more of SEQ ID NOS:15-55, wherein Xaa is any amino acid. There are numerous ways to combine SEQ ID NOS:14-55 into homopolymeric or heteropolymeric ligands. Furthermore, there are numerous ways to combine additional partial sequences of SEQ ID NOS:7-13 with each other and with SEQ ID NOS:14-55 to make polymeric ligands.

The polyligands of the invention optionally comprise spacer amino acids before, after, or between monomers. SEQ ID NO:1 is an embodiment of a polyligand of the structure A-S1-B-S2-C-S3-D, wherein A is SEQ ID NO:22, B is SEQ ID NO:54, C is SEQ ID NO:24, and D is SEQ ID NO:31, wherein Xaa is alanine, and wherein S1, S2, and S3 are spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

Monomeric ligands can be categorized into types. One type of monomeric ligand is a polypeptide where at least a portion of the polypeptide is capable of being recognized by mTOR as a substrate or pseudosubstrate (active site blocker). The portion of the polypeptide capable of recognition is termed the recognition motif. In the present invention, recognition motifs can be natural or synthetic. Examples of recognition motifs are well known in the art and include, but are not limited to, naturally occurring mTOR substrates and pseudosubstrate motifs (SEQ ID NOS:14-55 and partial sequences of SEQ ID NOS:7-13 containing a recognition motif). Another type of monomeric ligand is a polypeptide where at least a portion of the polypeptide is capable of associating with mTOR at a substrate or pseudosubstrate docking site (docking site blocker). A docking site type of monomeric ligand prevents mTOR substrate phosphorylation by interfering with substrate association and alignment.

A polymeric ligand comprises two or more monomeric ligands linked together.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclese activity. The flanking sequences optionally provide unique cloning sites within a vector and optionally provide directionality of subsequence cloning. Further, the nucleic acids of the invention are optionally incorporated into vector polynucleotides. The ligands, polyligands, and poly-nucleotides of this invention have utility as research tools and/or therapeutics.

DETAILED DESCRIPTION OF THE INVENTION

The present invention relates to ligands and polyligands that are mTOR modulators. Various embodiments of ligands and polyligands are represented in SEQ ID NOS:1-55. Polyligands are chimeric ligands comprising two or more monomeric polypeptide ligands. An example of a monomeric ligand is the polypeptide represented by SEQ ID NO:30, wherein Xaa is any amino acid. SEQ ID NO:30 is a selected subsequence of wild-type full length SEQ ID NO:7, wherein the amino acid corresponding to Xaa in the wild-type sequence is a serine or threonine phosphorylatable by mTOR. Another example of a monomeric ligand is the polypeptide represented by SEQ ID NO:55. Another example of a monomeric ligand is the polypeptide represented by SEQ ID NO:46. Each of SEQ ID NOS:14-55 represents an individual polypeptide ligand in monomeric form, wherein Xaa is any amino acid. SEQ ID NOS:14-55 are selected examples of subsequences (partial sequences) of SEQ ID NOS:7-13, however, other partial sequences of SEQ ID NOS:7-13 containing a recognition motif may also be utilized as monomeric ligands. Monomeric ligand subsequences of SEQ ID NOS:7-13 may be wild-type subsequences. Additionally, monomeric ligand subsequences of SEQ ID NOS:7-13 may have the mTOR phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:14-55. Furthermore, monomeric ligands and polyligands may have at least about 80%, 85%, 90%, 95%, 96%, 97%, 98% and 99% sequence identity to a subsequence of SEQ ID NOS:7-13.

An example of a homopolyligand is a polypeptide comprising a dimer or multimer of SEQ ID NO:24, wherein Xaa is any amino acid. Another example of a homopolyligand is a polypeptide comprising a dimer or multimer of SEQ ID NO:17, wherein Xaa is any amino acid.

An example of a heteropolyligand is a polypeptide comprising SEQ ID NO:55 and one or more of SEQ ID NOS:14-54, wherein Xaa is any amino acid. There are numerous ways to combine SEQ ID NOS:14-55 into homopolymeric or heteropolymeric ligands. Furthermore, there are numerous ways to combine additional partial sequences of SEQ ID NOS:7-13 with each other and with SEQ ID NOS:14-55 to make polymeric ligands.

Polyligands may comprise any two or more of SEQ ID NOS:14-55, wherein Xaa is any amino acid. SEQ ID NOS:14-55 are selected examples of partial sequences of SEQ ID NOS:7-13, however, additional partial sequences, wild-type or mutated, may be utilized to form polyligands. The instant invention is directed to all possible combinations of homopolyligands and heteropolyligands without limitation.

SEQ ID NOS:7-13 show proteins that contain at least one serine or threonine residue phosphorylatable by mTOR, the positions of which are represented by Xaa. Since mTOR autophosphorylates, mTOR itself is included as a substrate. SEQ ID NOS:14-55 are partial sequences of SEQ ID NOS:7-13 where, again, the locations of the mTOR phosphorylatable residues are represented by Xaa. In nature, Xaa is, generally speaking, serine or threonine. In one embodiment of the instant invention, Xaa can be mutated to any amino acid. Ligands where Xaa is serine or threonine can be used as part of a polyligand, however in one embodiment, at least one phosphorylatable serine or threonine is replaced with or mutated to another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the mTOR phosphorylatable serine(s) or threonine(s) are replaced by alanine. The ligands and polyligands of the invention are designed to modulate the endogenous effects of mTOR.

In general, ligand monomers based on natural mTOR substrates are built by isolating a putative mTOR phosphorylation recognition motif in a mTOR substrate. Sometimes it is desirable to modify or mutate the phosphorylatable residue to an amino acid other than serine or threonine. Additional monomers include the mTOR recognition motif as well as amino acids adjacent and contiguous on either side of the mTOR recognition motif. Monomeric ligands may therefore be any length provided the monomer includes the mTOR recognition motif. For example, the monomer may comprise an mTOR recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of mTOR comprising at least one copy of a peptide selected from the group consisting of:

a) a peptide at least 80% identical to a peptide comprising amino acid residues corresponding to amino acid residues 406-415 of SEQ ID NO:7, wherein the amino acid residue corresponding to amino acid residue 412 of SEQ ID NO:7 is an amino acid residue other than serine or threonine;

b) a peptide at least 80% identical to a peptide comprising amino acid residues corresponding to amino acid residues 405-418 of SEQ ID NO:7, wherein the amino acid residue corresponding to amino acid residue 412 of SEQ ID NO:7 is an amino acid residue other than serine or threonine;

c) a peptide at least 80% identical to a peptide comprising amino acid residues corresponding to amino acid residues 402-423 of SEQ ID NO:7, wherein the amino acid residue corresponding to amino acid residue 412 of SEQ ID NO:7 is an amino acid residue other than serine or threonine; and d) a peptide at least 80% identical to a peptide comprising amino acid residues corresponding to amino acid residues 399-424 of SEQ ID NO:7, wherein the amino acid residue corresponding to amino acid residue 412 of SEQ ID NO:7 is an amino acid residue other than serine or threonine.

In another embodiment, the invention encompasses an inhibitor of mTOR selected from the group consisting of
   a) a polypeptide comprising a partial sequence of SEQ ID NO:7, wherein the partial sequence includes a mutation of at least one amino acid residue at a position corresponding to amino acid residue 412.
   b) a polypeptide comprising a partial sequence of SEQ ID NO:8, wherein the partial sequence includes a mutation of at least one amino acid residue at a position corresponding to amino acid residue 401.
   c) a polypeptide comprising a partial sequence of SEQ ID NO:9, wherein the partial sequence includes a mutation of at least one amino acid residue at a position corresponding to amino acid residue 36, 45, 64, 69, and/or 82,
   d) a polypeptide comprising a partial sequence of SEQ ID NO: 10, wherein the partial sequence includes a mutation of at least one amino acid residue at a position corresponding to amino acid residue 37 and/or 46.
   e) a polypeptide comprising a partial sequence of SEQ ID NO:11, wherein the partial sequence includes a mutation of at least one amino acid residue at a position corresponding to amino acid residue 727.
   f) a polypeptide comprising a partial sequence of SEQ ID NO:12, wherein the partial sequence includes a mutation of at least one amino acid residue at a position corresponding to amino acid residue 307.

g) a polypeptide comprising a partial sequence of SEQ ID NO:13, wherein the partial sequence includes a mutation of at least one amino acid residue at a position corresponding to amino acid residue 2481.

As used herein, the terms "correspond(s) to" and "corresponding to," as they relate to sequence alignment, are intended to mean enumerated positions within a reference protein, e.g., p70S6K (SEQ ID NO:7), and those positions that align with the positions on the reference protein. Thus, when the amino acid sequence of a subject peptide is aligned with the amino acid sequence of a reference peptide, e.g., SEQ ID NO:7, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for mTOR, such as substrates identified by SEQ ID NOS:7-13. Furthermore, if the substrate has more than one recognition motif, then more than one monomer may be identified therein.

Another embodiment of the invention is a nucleic acid molecule comprising a polynucleotide sequence encoding at least one copy of a ligand peptide.

Another embodiment of the invention is an isolated polypeptide homopolyligand, wherein the homopolyligand modulates mTOR activity.

Another embodiment of the invention is an isolated polypeptide heteropolyligand, wherein the heteropolyligand modulates mTOR activity.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting mTOR in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring mTOR recognition motif that has been modified by addition, deletion, or substitution of one or more amino acids in the primary structure (amino acid sequence) of the motif. For example, a modified mTOR recognition motif may be a motif where the phosphorylatable amino acid has been modified to a non-phosphorylatable amino acid. The terms "protein," "peptide" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques, (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carrillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length-0, Cutoff Score-1, Gap Penalty-5, Gap Size Penalty 0.05, Window Size-500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of amino acids of the query sequence that are N- and C-terminus to the reference sequence that are not matched/aligned, as a percent of the total amino acids of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Specific examples of spacers used between monomers in SEQ ID NO: 1 are the four amino acid spacers PAAA and PAGA, and the six amino acid spacer EFPGGG. In the instance of SEQ ID NO:1, the proline-containing spacer is intended to break an alpha helical secondary structure. Spacer amino acids may be any amino acid and are not limited to these alanine, glycine, and proline-containing examples. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG™ (Kodak; Rochester, N.Y.), HA (hemagluttinin), c-Myc and His6. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Pepetides can also be synthesized utilizing non-automated peptide sythesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics. For example, ligands depicted generically in FIGS. 7A-7G represent ligands with utility as subcellular tools or therapeutics. mTOR ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10B:
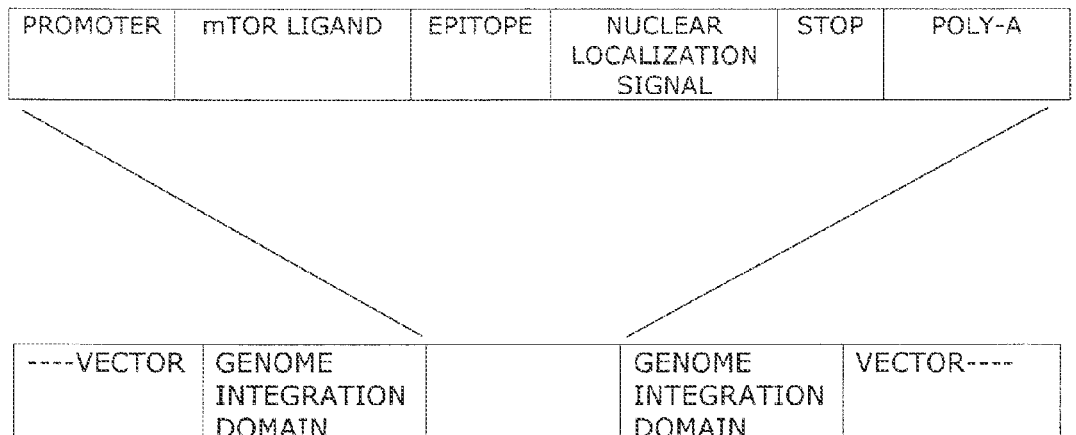
Figure 10C:
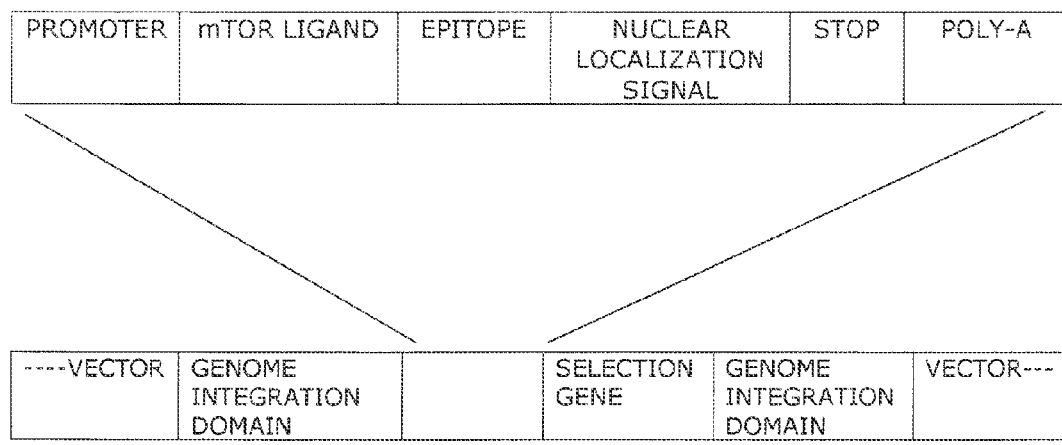

FIG. 10A shows a vector containing an mTOR ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
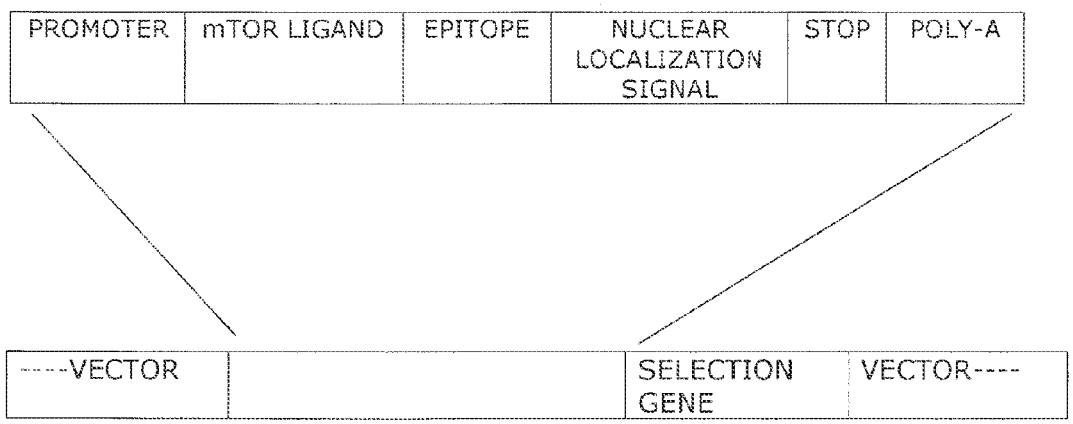

FIG. 10D shows a vector containing an mTOR ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Sites for cleavage by other restriction enzymes, including horning endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealled. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, RheoSwitch® is an inducible promoter system available from RheoGene. Temperature sensitive promotors can also be used to increase or decrease gene expression. An embodiment of the invention comprises a ligand or polyligand gene construct whose expression is controlled by an inducible promoter. In one embodiment, the inducible promotor is tetracycline controllable.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished, by exploiting the natural properties of restriction endonuclease site recognition and cleavage. One aspect of the invention, encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
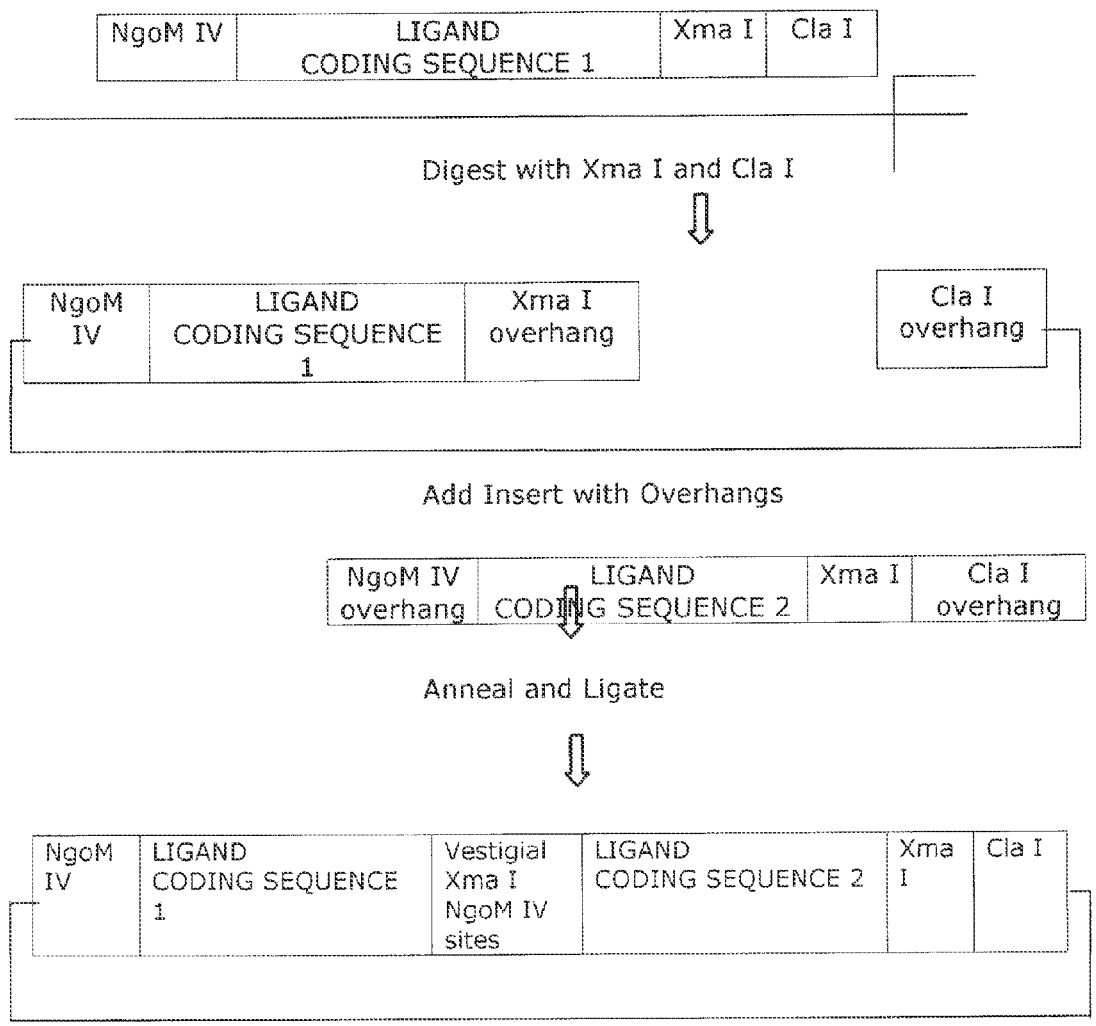
FIG. 11 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to firm a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM TV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate mTOR activity are disclosed, Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

Assays.

Ligands of the invention are assayed for kinase modulating activity using one or more of the following exemplary methods.

Method 1.

A biochemical assay is performed employing commercially-obtained kinase, commercially-obtained substrate, commercially-obtained kinase inhibitor (control), and semi-purified inhibitor ligand of the invention (decoy ligand). Ligands (also referred to herein as decoy ligands) are linked to an epitope tag at one end of the polypeptide for purification and/or immobilzation, for example, on a microtiter plate. The tagged decoy ligand is made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence is employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane Cold Spring Harbor Laboratory Press, 1999).

For example, tagged decoy ligand synthesized using an in vitro transcription/translation system is semi-purified and added to a microtiter plate containing kinase enzyme and substrate immobilized by an anti-substrate specific antibody. Microtiter plates are rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 mm. The Control experiments include absence of kinase enzyme, and/or absence of decoy ligand, and/or presence/absence of known kinase inhibitors. A known kinase inhibitor useful in the assay is staurosporine.

Method 2.

A similar assay is performed employing the same reagents as above but the substrate is biotinylated and immobilized by binding to a streptavidin-coated plate.

Method 3.

A biochemical assay is performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, is then added to measure kinase activity.

For example, tagged decoy ligand synthesized using an in vitro transcription/translation system is semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is related to kinase activity. Control experiments include absence of kinase enzyme, and/or absence of decoy ligand, and/or presence/absence of known kinase inhibitors. A known kinase inhibitor useful in the assay is staurosporine.

Method 4.

A similar cell-based assay is performed employing same reagents as above, but synthesizing the decoy ligand in a mammalian cell system instead of an in vitro transcription/translation system. Decoy ligands are linked to an epitope tag at one end of the polypeptide for immobilzation and/or for purification and/or for identification in a western blot. Optionally, tagged decoy ligands are also linked to a cellular localization signal for phenotypic comparison of pan-cellular and localized kinase modulation. A vector polynucleotide comprising a constitutive promotor, such as the CMV promotor, a decoy ligand coding sequence, an epitope tag coding sequence, and optionally a localization signal coding sequence is employed to express the decoy ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and immunoreagent-containing methods are performed as described in: Using Antibodies: A Laboratory Manual (Harlow and Lane Cold Spring Harbor Laboratory Press, 1999).

EXAMPLES

Example 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

Example 2

A transgene is constructed using a cytomegalovirus (CMV) promoter to direct expression of a fusion protein comprising SEQ ID NO:22, SEQ ID NO:24, SEQ NO:37, wherein Xaa is alanine (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode an mTOR ligand, a FLAG™ epitope, and a nuclear localization signal. The mTOR ligand is a monomeric ligand, homopolymeric ligand or heteropolymeric ligand as described herein.

Nucleotide sequences encoding a FLAG™ epitope are placed downstream of nucleotide sequences encoding the mTOR ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

Example 4

Modulation of mTOR cellular function by subcellularly localized mTOR polyligand is illustrated. A transgene construct containing nucleic acids that encode a polyligand fusion protein, epitope, and endoplasmic reticulum localization signal is made. The expression unit contains nucleotides that encode SEQ ID NO:1 (POLYLIGAND), a c-Myc epitope (EPITOPE), and a nuclear localization signal (LOCALIZATION SIGNAL). This expression unit is subsequently subcloned into a vector between a EF1alpha promoter and an SV40 polyadenylation signal. The completed transgene-containing expression vector is then used to transfect cells. Inhibition of mTOR activity is demonstrated by measuring phosphorylation of endogenous substrates against controls and/or observing phenotypes.

Example 5

Ligand function and localization is demonstrated in vivo by making a transgene construct used to generate mice expressing a ligand fusion protein targeted to the nucleus. The transgene construct is shown generically in FIG. 10B. The expression unit contains nucleotides that encode a tetramer of SEQ ID NO:33, a hemagluttinin epitope, and a nuclear localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 5 harbor the transgene in their genomes.

Test 2: Tissue homogenates are prepared for Western blot analysis. This experiment demonstrates the transgene is expressed in tissues of transgenic mice because hemaglutinin epitope is detected in transgenic homogenates but not in non-transgenic homogenates.

Test 3: Function is assessed by phenotypic observation or analysis against controls after induction of expression.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate mTOR activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polynucleotide comprising a nucleotide sequence encoding a polypeptide heteropolyligand, wherein a heteropolyligand monomer therein is an amino acid sequence at least 97% identical to any one of SEQ ID NO: 37, wherein Xaa is any amino acid, and wherein said polypeptide heteropolyligand inhibits mTOR activity.

2. A host cell comprising the isolated polynucleotide of claim 1.

3. The isolated polynucleotide of claim 1 operably linked to a promoter.

4. The isolated polynucleotide of claim 3, wherein the promoter is an inducible promoter.

5. The isolated polynucleotide of claim 1, wherein the polynucleotide is flanked on one end by a sequence cleavable by NgoM IV, and wherein the polynucleotide is flanked on the other end by sequences cleavable by Xma I and Cla I.

6. A method of inhibiting mTOR in a cell, the method comprising:
 (a) transfecting a vector comprising the isolated polynucleotide of claim 1 into a host cell; and
 (b) culturing the transfected host cell under conditions suitable to produce at least one copy of the polypeptide heteropolyligand,
 wherein said polypeptide heteropolyligand inhibits mTOR activity.

7. The isolated polynucleotide of claim 1, wherein the heteropolyligand monomer is an amino acid sequence at least 98% identical to SEQ ID NO: 37.

8. The isolated polynucleotide of claim 1, wherein the heteropolyligand monomer is an amino acid sequence at least 99% identical to SEQ ID NO: 37.

9. The isolated polynucleotide of claim 1, wherein the heteropolyligand monomer comprises the amino acid sequence of SEQ ID NO: 37.

10. The isolated polynucleotide of claim 1, wherein the heteropolyligand is linked to one or more of a localization signal, an epitope tag, or a reporter.

11. A vector comprising the isolated polynucleotide of claim 1.

12. A vector comprising the isolated polynucleotide of claim 3.

13. A vector comprising the isolated polynucleotide of claim 4.

14. A vector comprising the isolated polynucleotide of claim 5.

15. A vector comprising the isolated polynucleotide of claim 7.

16. A vector comprising the isolated polynucleotide of claim 8.

17. A vector comprising the isolated polynucleotide of claim 9.

18. A vector comprising the isolated polynucleotide of claim 10.

19. The isolated polynucleotide of claim 1, wherein at least one amino acid designated as Xaa is alanine.

20. The isolated polynucleotide of claim 1, wherein at least one amino acid designated as Xaa is an amino acid other than serine or threonine.

* * * * *